US006365749B1

(12) United States Patent
Kim et al.

(10) Patent No.: US 6,365,749 B1
(45) Date of Patent: *Apr. 2, 2002

(54) PROCESS FOR THE PREPARATION OF RING-OPENED EPOTHILONE INTERMEDIATES WHICH ARE USEFUL FOR THE PREPARATION OF EPOTHILONE ANALOGS

(75) Inventors: Soong-Hoon Kim; Robert M. Borzilleri, both of Lawrenceville, NJ (US)

(73) Assignee: Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,582

(22) Filed: Oct. 13, 1998

Related U.S. Application Data

(60) Provisional application No. 60/067,550, filed on Dec. 4, 1997.

(51) Int. Cl.[7] ...................... C07D 277/30; C07D 493/04
(52) U.S. Cl. ...................................................... 548/204
(58) Field of Search ........................................ 548/204

(56) References Cited

U.S. PATENT DOCUMENTS

| | | | |
|---|---|---|---|
| 6,194,181 B1 | 2/2001 | Hofmann et al. | 435/118 |
| 6,204,388 B1 | 3/2001 | Danishefsky et al. | 546/340 |
| 6,211,412 B1 | 4/2001 | Georg et al. | 568/309 |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | WO 93/10121 * | 5/1993 |
| WO | 97/19086 | 5/1997 |
| WO | 98/08849 | 3/1998 |
| WO | 98/22461 | 5/1998 |
| WO | WO 9822461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | WO 99/39694 | 8/1999 |
| WO | WO 9942602 | 8/1999 |
| WO | WO 9943320 | 9/1999 |
| WO | WO 99/43653 | 9/1999 |
| WO | WO 99/67252 | 12/1999 |
| WO | WO 00/00485 | 1/2000 |
| WO | WO 0031247 | 6/2000 |
| WO | WO 00/37473 | 6/2000 |
| WO | WO 00/49021 | 8/2000 |
| WO | WO 00/66589 | 11/2000 |

OTHER PUBLICATIONS

Balog, A., et al., "Total Synthesis of (–)-Epothilone A", *Angew. Chem. Int. Ed. Engl.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothiones, A New Class of Microtuble–stabilizing Agents with a Taxol–like Mechanism of Action", *Cancer Res.* 55, No. 11, 2325–2333 (1995).

Fujisawa, T., et al., "Deoxygenation of Epoxides to Olefins with $FeCl_3$—n–BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

Gladysz, J. A., et al., "Deoxygenation of Epoxides by Metal Atom Cocondensation", *J. Org. Chem.*, vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hofle, G., et al., "N–Oxidation of Epothilone A–C and O–Acyl Rearrangement to C–19 to C–21—Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski, R. J. et al., "Actitivies of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

(List continued on next page.)

*Primary Examiner*—Bruck Kifle
(74) *Attorney, Agent, or Firm*—Rena Patel

(57) ABSTRACT

The present invention relates to a process to produce ring opened epothilones and the novel ring opened epothilones produced therefrom.

3 Claims, No Drawings

OTHER PUBLICATIONS

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygeneration", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium ($TiCl_3$/$LiAlH_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et. al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5$/$NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., "Reduction and Isomerization of Oxiranes and Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6, No. 7, 893–898 (1996).

Winkler, J. D., et al., "A Model For The Taxol (Paclitaxel)/Epothilone Pharmacophore", *Biorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1 / 2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtuble–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", *J. Org. Chem.*, vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schnizer, D., et al., "Studies Towards the Total Synthesis of Epothilones: Asymmetric Synthesis of the Key Fragments", *Chem. Eur. J.,* vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* vol. 38, No. 12, 2061–2064 (1997).

Schnizer, D., et al., "Syntheses of (–)–Epothilone A", *Chem. Eur. J.,* vol. 5, No. 9, 2483–2491 (1999).

Schinzer, D., et al., "Syntheses of (–)–Epothilone B", *Chem. Eur. J.,* vol. 5, No. 9, 2492–2500 (1999).

Nicolaou, K. C., et al., "Synthesis and Biological Properties of C12, 13–Cyclopropylepothilone A and Related Epothilones", *Chemistry & Biology,* vol. 5, No. 7, 365–372 (1998).

Altmann et al., 2000, "Epothilones and Related Structures–A New Class of Microtubule Inhibitors with Potent In Vivo Antitumor Activity", Biochim. Biophys. Acta, 1470:M79–M81.

Nicolaou et al., 1998, "Total Synthesis of Epothilone E and Analogs with Modified Side Chains Through the Stille Coupling Reaction", Angew. Chem. Int. Ed. 37: 84–87.

Nicolaou et al., 1998, "Chemistry and Biology of Epothilones", Angew. Chem. Int. Ed. 37:2014–2045.

* cited by examiner

PROCESS FOR THE PREPARATION OF RING-OPENED EPOTHILONE INTERMEDIATES WHICH ARE USEFUL FOR THE PREPARATION OF EPOTHILONE ANALOGS

This application claims priority from U.S. Provisional Application No. 60/067,550, filed Dec. 4, 1997.

BRIEF DESCRIPTION OF THE INVENTION

The present invention is directed to a process for preparing compounds of the formula I.

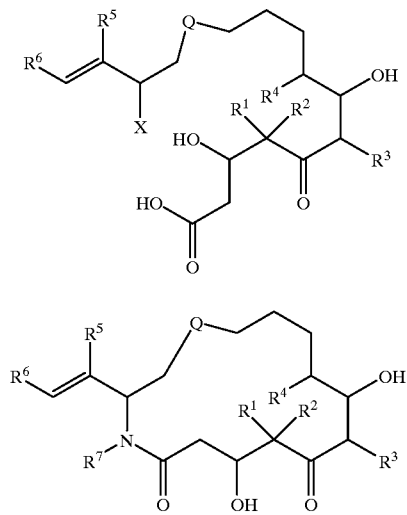

The compounds of formula I are novel intermediates for the preparation of epothilone analogs which are useful in the treatment of a variety of cancers and other abnormal proliferative diseases. Compounds of the formula I may be used to prepare, for example, analogs of the formula II which are anticancer agents. As used in the formulas I, II, and throughout the specification, the symbols have the following meanings:

X is $NR^7R^8$, $N_3$, $N(COR^{11}) COR^{12}$ and $NR^9SO_2R^{10}$

Q is selected from the group consisting of

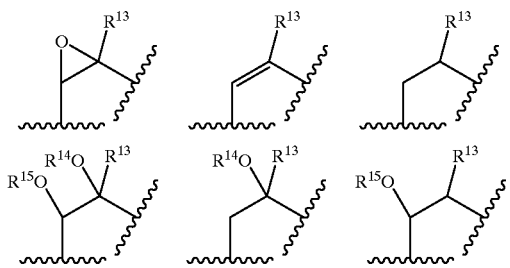

$R^1$, $R^2$, $R^3$, $R^4$, $R^5$, $R^{13}$, $R^{14}$, and $R^{15}$ are selected from the group H, alkyl, substituted alkyl, or aryl and when $R^1$ and $R^2$ are alkyl can be joined to form a cycloalkyl;

$R^8$ is H, alkyl, substituted alkyl, aryl, substituted aryl, o-alkyl or o-substituted alkyl; $R^6$, $R^7$, and $R^9$ are selected from the group consisting of H, alkyl, substituted alkyl, aryl, cycloalkyl, or heterocyclo $R^{10}$, $R^{11}$ and $R^{12}$ are alkyl, substituted alkyl, aryl or substituted aryl and $R^{11}/R^{12}$ can join together to form a nitrogen containing ring e.g. phthalimido.

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy. The substituent may be further substituted by halo, hydroxy, alkyl, alkoxy, aryl, substituted aryl, substituted alkyl or aralkyl.

The term "cycloalkyl" refers to an optionally substituted, saturated cyclic hydrocarbon ring system, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofliryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl.

Exemplary substituents include one or more alkyl groups as described above or one or more groups described above as alkyl substituents. Also included are smaller heterocyclos, such as, epoxides and aziridines.

The term "heteroatoms" shall include oxygen, sulfur and nitrogen.

Use and Utility

The compounds of formula II are microtubule-stabilizing agents. They are thus useful in the treatment of a variety of cancers, including (but not limited to) the following;
carcinoma, including that of the bladder, breast, colon, kidney, liver, lung, ovary, pancreas, stomach, cervix, thyroid and skin; including squamous cell carcinoma;
hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;
hematopoietic tumors of myeloid lineage, including acute and chronic myelogenous leukemias and promyelocytic leukemia;
tumors of mesenchymal origin, including fibrosarcoma and rhabdomyoscarcoma;
other tumors, including melanoma, seminoma, tetratocarcinoma, neuroblastoma and glioma;
tumors of the central and peripheral nervous system, including astrocytoma, neuroblastoma, glioma, and schwannomas;
tumors of mesenchymal origin, including fibrosarcoma, rhabdomyoscaroma, and osteosarcoma; and
other tumors, including melanoma, xenoderma pigmentosum, keratoactanthoma, seminoma, thyroid follicular cancer and teratocarcinoma.

Compounds of formula II may also inhibit tumor angiogenesis, hereby affecting the growth of tumors. Such anti-angiogenesis roperties of the compounds of formula II may also be useful in the treatment of certain forms of blindness related to retinal vascularization, arthritis, especially inflammatory arthritis, multiple sclerosis, restinosis and psoriasis.

Compounds of formula II may induce or inhibit apoptosis, a physiological cell death process critical for normal development and homeostasis. Alterations of apoptotic pathways contribute to the pathogenesis of a variety of human diseases. Compounds of formula II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The novel compounds of formula I may exist as multiple optical geometric and stereoisomers. Included within the present invention are all such isomers and mixtures thereof in the racemic form.

The compounds of the present invention are novel intermediates to produce the compounds of formula II which are anticancer agents. Also novel is the process to produce the compounds of formula I.

Method of Preparation

Compounds of formula I are prepared as shown in Scheme 1. A compound of formula III can be treated with a palladium catalyst, such as palladium tetrakistriphenylphosphine, and a "soft" nucleophile to provide a compound of formula I where X is $NR^7R^8$, $N_3$, $N(COR^{11})$ $COR^{12}$ and $NR^9$ or $NR^9$ $SO_2R^{10}$, (see for example: J. Tsuji, *Palladium Reagents and Catalysts: Innovations in Organic Synthesis,* New York: Wiley and Sons, 1995).

Compounds of formula III are known compounds, see, for example, HOFLE et al., Angew. Chem. Int. Ed. Engl. 1996, 35, No. 13/14; WO 93/10121 published May 27, 1993; WO 97/19086 published May 29, 1997; Nicolaou et al. Angew. Chem. Int. Ed. Engl., 1997, 36, 2097 and Danishefsky et al., Angew. Chem. Int. Ed. Engl., 1997, 36, 2093.

Scheme 1

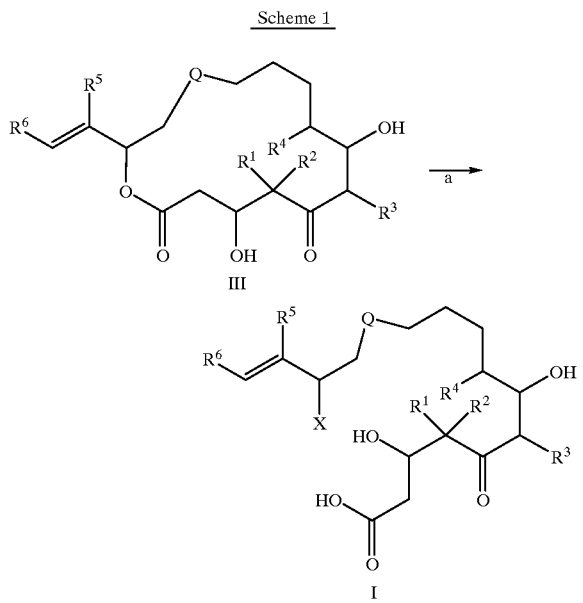

I

For example, a compound of formula I where X is $N_3$ (i.e., compound Ia) can be prepared from a compound of formula III by treatment with palladium tetrakistriphenylphosphine and azide donor, such as, a metal azide (eg. lithium or sodium azide) as shown in Scheme 2.

Scheme 2

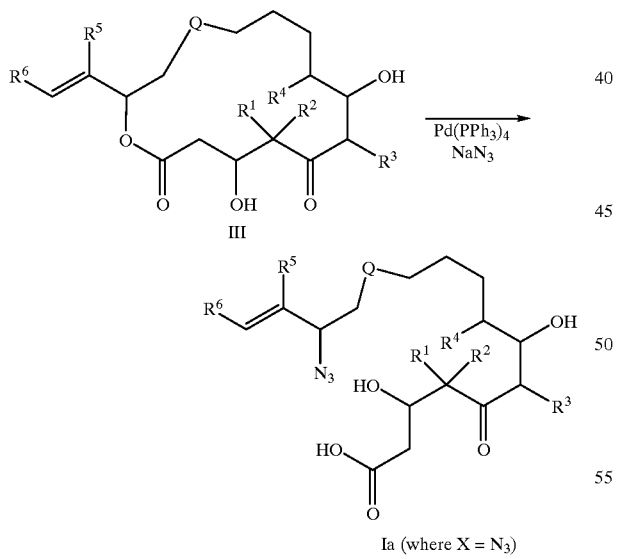

Ia (where X = $N_3$)

A compound of formula II can be prepared from a compound of formula Ia as shown in Scheme 3. A compound of formula Tb can be prepared from a compound of formula Ia by reduction with reducing agents such as triphenylphosphine or hydrogen and platinum oxide. A compound of formula II can be prepared from a compound of formula Ib by macrolactamization using a suitable coupling agent such as diphenylphosphoryl azide (for other macrolactamization agents, see: J. M. Humphrey and A. R. Chamberlin, *Chem. Rev.*, 97, 2243–2266 (1997)).

Scheme 3

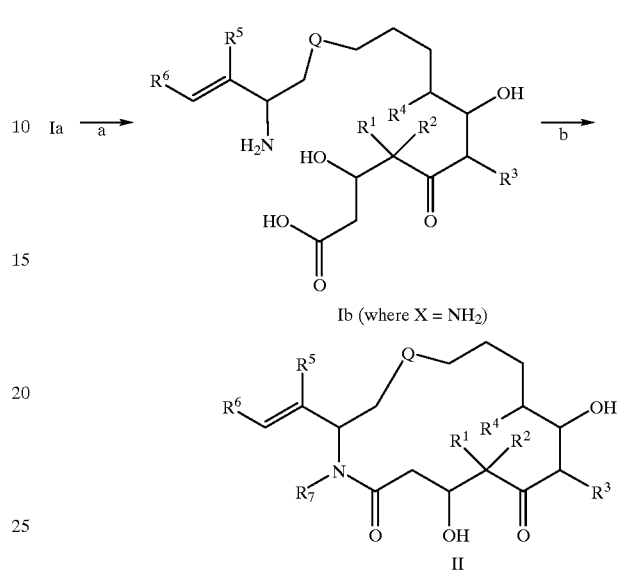

II

A compound of formula I where X is $NR^7R^8$ (i.e., compound Ic) can be prepared from a compound of formula III by treatment with palladium tetrakistriphenylphosphine and a primary or secondary amine as shown in Scheme 4.

Scheme 4

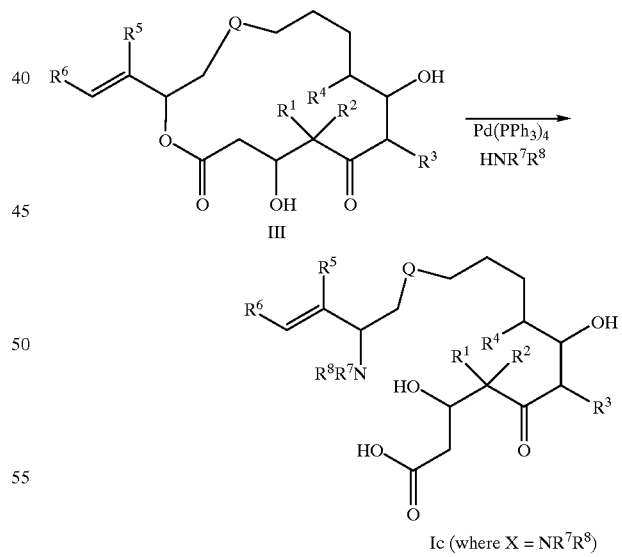

Ic (where X = $NR^7R^8$)

A compound of formula I where X is $NR^9SO_2R^{10}$ or $N(COR^{11})COR^{12}$ (i.e., compound Id and Ie) can be prepared from a compound of formula III by treatment with palladium tetrakistriphenylphosphine and a salt of the corresponding sulfonamide (i.e., $HNR^9SO_2R^{10}$) or imide (or $N(COR^{11})COR^{12}$) as shown in Scheme 5.

Scheme 5

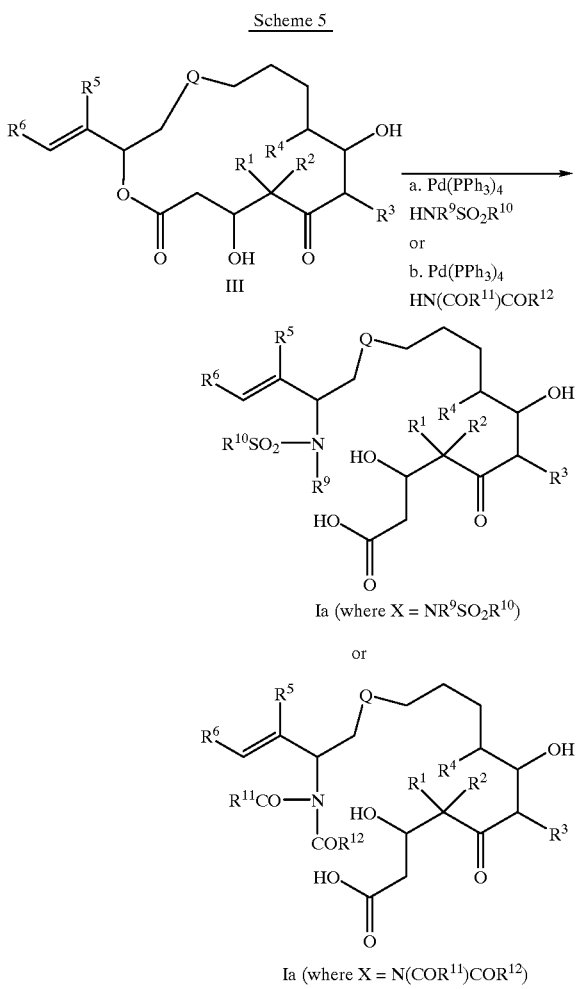

EXAMPLE 1

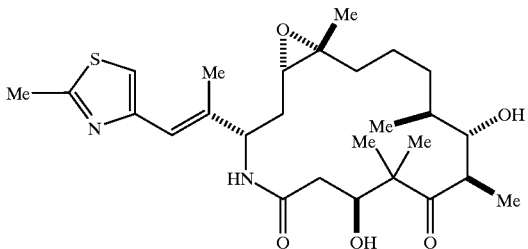

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4aza-17-oxabicyclo[14.1.0]heptadecane-5,9-dione A. (3S,6R,7S,8S,12R,13S,15S)-15-Azido-12,13-epoxy4,4,6,8,12,16-hexamethyl-7-hydroxy-17-(2-methyl-4-thiazolyl)-5-oxo-16-heptadecenoic acid A solution of epothilone B (0.35 g, 0.69 mmol) in degassed THF (4.5 mL) was treated with a catalytic amount (80 mg, 69 mmol) of tetrakis(triphenylphosphine) palladium (0) and the suspension was stirred at 25° C., under Ar for 30 min. The resulting bright yellow, homogeneous solution was treated all at once with a solution of sodium azide (54 mg, 0.83 mmol) in degassed $H_2O$ (2.2 mL). The reaction mixture was warmed to 45° C. for 1 h, diluted with $H_2O$ (5 mL) and extracted with EtOAc (4×7 mL). The organic extracts were washed with saturated aqueous NaCl (15 mL), dried ($Na_2SO_4$), and concentrated in vacuo. The residue was purified by flash chromatography ($SiO_2$, 3.0×15 cm, 95:5.0:0.5 $CHCl_3$—MeOH—AcOH) to afford Compound A (0.23 g, 61%) as a colorless oil. MS ($ESI^+$): 551 $(M+H)^+$; MS($ESI^-$): 549 $(M-H)^-$.

B. (3S,6B,7S,8S,12R,13S,15S)-15-Amino-12,13-epoxy-4,4,6,8,12,16-hexeamethyl-7-hydroxy-17-(2-methyl-4-thiazolyl)-5-oxo-16-heptadecenoic acid A solution of Compound A (0.23 g, 0.42 mmol) in THF (4.0 mL) was treated with $H_2O$ (23 mL, 1.25 mmol) and polymer supported triphenylphosphine (Aldrich, polystyrene cross-linked with 2% DVB, 0.28 g, 0.84 mmol) at 25° C. The resulting suspension was stirred at 25° C. under Ar (32 h), filtered through a Celite pad and concentrated in vacuo. The residue was purified by flash chromatography ($SiO_2$, 1.5×10 cm, 95:5.0:0.5 to 90:10:1.0 $CHCl_3$—MeOH—AcOH gradient elution) to afford Compound B (96 mg, 44%) as a colorless oil. MS ($ESI^+$): 525.2 $(M+H)^+$; MS($ESI^-$): 523.4 $(M-H)^-$.

Alternatively, to a 25 mL round-bottom flask charged with Compound A (0.26 g, 0.47 mmol) and PtO2 (0.13 g, 50 wt %) was added absolute EtOH under Ar. The resulting black mixture was stirred under one atmosphere of $H_2$ for 10 h, after which time the system was purged with $N_2$ and an additional portion of $PtO_2$ (65 mg, 25 wt %) was added. Once again the reaction mixture was stirred under a blanket of $H_2$ for 10 h. The system was then purged with $N_2$, and the reaction mixture was filtered through a Celite pad eluting with $CH_2Cl_2$ (3×25 mL). The solvents were removed in vacuo and the residue was purified as described above to afford Compound B (0.19 g, 75%).

Alternatively, a solution of Compound A (20 mg, 36 mmol) in THF (0.4 mL) was treated with triphenylphosphine (19 mg, 73 mmol) under Ar. The reaction mixture was warmed to 45° C., stirred for 14 h and cooled to 25° C. The resulting iminophosphorane was treated with ammonium hydroxide (28%, 0.1 mL) and once again the reaction mixture was warmed to 45° C. After 4 h, the volatiles were removed in vacuo and the residue was purified as described above to afford Compound B (13 mg, 70%).

C. [1S-[1R*,3R*(E),7R*,10R*,11S*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

A solution of Compound B (0.33 g, 0.63 mmol) in degassed DMF (250 mL) was treated with solid $NaHCO_3$ (0.42 g, 5.0 mmol) and diphenylphosphoryl azide (0.54 mL, 2.5 mmol) at 0° C. under Ar. The resulting suspension was stirred at 4° C. for 24 h, diluted with phosphate buffer (250 mL, pH=7) at 0° C. and extracted with EtOAc (5×100 mL). The organic extracts were washed with 10% aqueous LiCl (2×125 mL), dried ($Na_2SO_4$) and concentrated in vacuo. The residue was first purified by flash chromatography ($SiO_2$, 2.0×10 cm, 2–5% MeOH-$CHCl_3$ gradient elution) and then repurified using a Chromatotron (2 mm $SiO_2$ GF rotor, 2–5%

MeOH-CHCl₃ gradient elution) to afford the title compound (0.13 g, 40%) as a colorless oil: ¹H NMR (CDCl₃, 400 MHz) δ6.98 (s, 1 H), 6.71 (d, 1H, NH, J=8.1 Hz), 6.56 (s, 1 H), 4.69–4.62 (m, 1 H), 4.18–4.12 (m, 1 H), 4.01–3.96 (m, 1 H), 3.86 (s, 1 H), 3.38–3.34 (m, 1 H), 2.82 (dd, 1 H, J=5.6, 6.0 Hz), 2.71 (s, 3 H), 2.58 (s, 1 H), 2.43 (dd, 1 H, J=9.0, 14.5 Hz), 3.34 (dd, 1 H, J=3.0, 14.5 Hz), 2.14 (s, 3 H), 2.05–1.92 (m, 2 H), 1.82–1.41 (a series of multiplets, 7 H), 1.35 (s, 3 H), 1.28 (s, 3 H), 1.18 (d, 3 H, J=6.8 Hz), 1.14 (s, 3 H), 1.00 (d, 3 H, J=6.8 Hz); MS (ESI⁺): 507.2 (M+H)⁺; MS(ESI⁻): 505.4 (M−H)⁻.

EXAMPLE 2

[1S-[1R*,3R*(E),7R*,10S*,11R*,12R*,16S*]]-7,11-Dihydroxy-8,8,10,12,16-pentamethyl-3-[1methyl-2-(2-methyl-4-thiazolyl)ethenyl]-4-aza-17-oxabicyclo[14.1.0]heptadecane-5,9-dione Alternatively, compound 1C can be prepared as follows without isolation of intermediates. A suspension of epothilone B (5.06 g, 9.97 mmol) and sodium azide (0.777 g, 12.0 mmol) in a THF-H₂O mixture (5:1, 96 mL) was degassed for 15–20 min with nitrogen and then treated with a catalytic amount (1.2 g, 0.997 mmol) of tetrakis (triphenylphosphine) palladium (0) under Ar. The reaction mixture was warmed to 45° C. for min and cooled to 25° C.

The resulting bright yellow homogeneous solution was directly treated with a 1.0 M solution of trimethylphosphine in THF (24.9 mL, 24.9 mmol) at 25° C. and the reaction mixture was stirred for 1–2 hr at ambient temperature.

The amino acid-containing mixture was then diluted with MeCN-DMF (20:1, 450 mL), cooled to 0° C. and treated with 1-hydroxybenzotriazole hydrate (1.35 g, 9.97 mmol) followed by 1-(3-dimethylaminopropyl)-3-ethylcarbodiimide hydrochloride (4.78 g, 24.9 mmol). The reaction mixture was warmed to 25° C., stirred for 12 hr and extracted with EtOAc (4×200 mL). The organic extracts were washed with H₂O (400 mL), saturated aqueous NaHCO₃ (400 mL), and saturated aqueous NaCl (400 mL). The organic extracts were dried (Na₂SO₄) and concentrated in vacuo. The residue was purified by flash chromatography (SiO₂, 5.0×25 cm, 2% MeOH-CHCl₃) and then HPLC (YMC S-15 ODS 50×500 mm column, 38 to 95% MeCN/H₂O, gradient (40 min), 50 mL/min flow rate). The appropriate fractions were concentrated in vacuo and the residue was lyophilized from aqueous acetonitrile to afford the title compound (0.998 g, 20%), as a white lyopholizate. MS (ESI⁺): 507.2 (M+H)⁺; MS(ESI⁻): 505.4 (M−H)⁻.

What is claimed is:

1. A compound of the formula

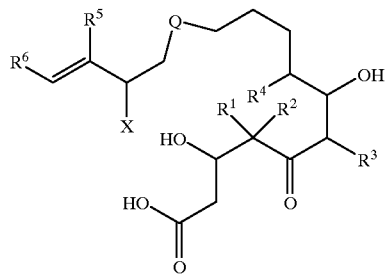

wherein

X is selected from the group consisting of $N_3$, $NR^7R^8$, $N(COR^{11})COR^{12}$ and $NR^9SO_2R^{10}$;

Q is selected from the group consisting of

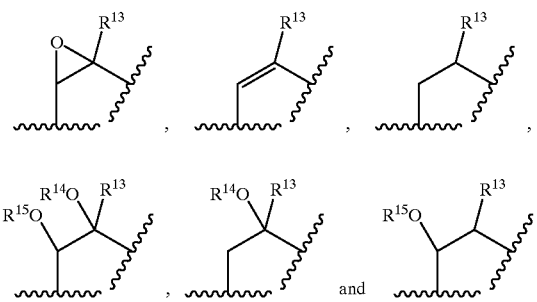

$R^1, R^2, R^3, R^4, R^5, R^{13}, R^{14}$, and $R^{15}$ are selected from the group consisting of H, alkyl, substituted alkyl, and aryl, and when $R^1$ and $R^2$ are alkyl can be joined to form a cycloalkyl;

$R^8$ is selected from the group consisting of H, alkyl, substituted alkyl, aryl, substituted aryl, O-alkyl, and O-substituted alkyl;

$R^6$, $R^7$ and $R^9$ are selected from the group consisting of H, alkyl, substituted alkyl, aryl, cycloalkyl, and 4 to 7 membered ring systems having 1, 2, or 3 heteroatoms, wherein the heteroatoms are independently nitrogen, oxygen, or sulfur; and $R^{10}$, $R^{11}$, $R^{12}$ are selected from the group consisting of alkyl, substituted alkyl, aryl and substituted aryl, and when X is $N(COR^{11})COR^{12}$, the $R^{11}$ and $R^{12}$ groups therein can join together to form a mono or bicyclic ring.

2. A process to produce a compound of the formula

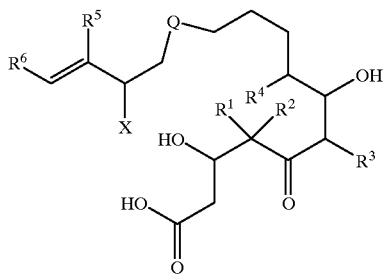

wherein

X is selected from the group consisting of $N_3$, $NR^7NR^8$, $N(COR^{11})COR^{12}$ and $NR^9SO_2R^{10}$;

Q is selected from the group consisting of

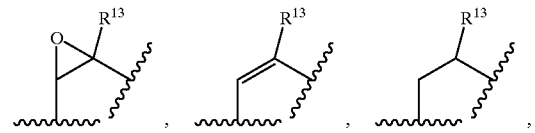

-continued

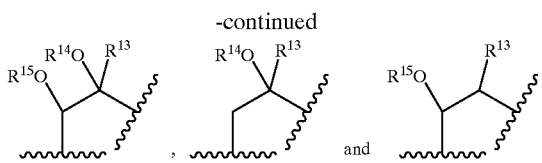

$R^1, R^2, R^3, R^4, R^5, R^{13}, R^{14}$ and $R^{15}$ are selected from the group consisting of H, alkyl, substituted alkyl, and aryl, and when $R^1$ and $R^2$ are alkyl can be joined to form a cycloalkyl;

$R^8$ is selected from the group consisting of H, alkyl, substituted alkyl, aryl, substituted aryl, O-alkyl, and O-substituted alkyl;

$R^6$, $R^7$ and $R^9$ are selected from the group consisting of H, alkyl, substituted alkyl, aryl, cycloalkyl, and 4 to 7 membered ring systems having 1, 2, or 3 heteroatoms, wherein the heteroatoms are independently nitrogen, oxygen, or sulfur;

$R^{10}$, $R^{11}$, $R^{12}$ are selected from the group consisting of alkyl, substituted alkyl, aryl and substituted aryl, and when X is $N(COR^{11})COR^{12}$, the $R^{11}$ and $R^{12}$ groups therein can join together to form a mono or bicyclic ring, which comprises reacting a compound of the formula

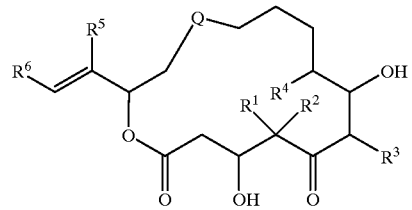

with a palladium catalyst in the presence of a nucleophilic donor.

3. The compound of the formula:
(3S,6R,7S,8S,12R,13S,15S)-15-Amino-12,13-epoxy-4,4,6,8,12,16-hexamethyl-7-hydroxy-17-(2-methyl-4-thiazoyl)-5-oxo-16-heptadecenoic acid.

* * * * *